United States Patent [19]

Carestio et al.

[11] 4,264,069

[45] Apr. 28, 1981

[54] THERAPEUTIC APPARATUS

[76] Inventors: Paul V. Carestio, 194 Franklin St., Lackawanna, N.Y. 14218; David J. Pienta, 238 Velore St., Orchard Park, N.Y. 14127

[21] Appl. No.: 932,119

[22] Filed: Aug. 9, 1978

[51] Int. Cl.[3] ............................................ A61F 9/00

[52] U.S. Cl. ........................................ 272/93; 351/2; 351/23; 128/745

[58] Field of Search .............. 272/93; 273/106 B, 100, 273/104; 128/745, 303.1, 76.5; 351/17, 23, 2

[56] References Cited

U.S. PATENT DOCUMENTS

| | | | |
|---|---|---|---|
| 1,501,942 | 7/1924 | Carman | 273/100 |
| 1,650,768 | 11/1927 | Reaves | 351/17 |
| 1,705,501 | 3/1929 | Sas | 273/100 |
| 3,947,023 | 3/1976 | Martin | 272/93 |

FOREIGN PATENT DOCUMENTS

| | | | |
|---|---|---|---|
| 16849 | of 1897 | United Kingdom | 273/100 |

*Primary Examiner*—Richard J. Johnson
*Attorney, Agent, or Firm*—Christel, Bean & Linihan

[57] ABSTRACT

Therapeutic apparatus comprising a supporting base adapted to rest on a floor or similar surface and including three arm members each releasably connected at one end to an arcuate connecting member at spaced locations therealong, all disposed in substantially the same place. The arm members define angles therebetween, the sizes of which are indicated visually by elements spaced along the connecting member. A number of pole elements are associated with the arm members each being releasably connected at one end to an arm member and all the pole elements extending in the same direction at substantially right angles to the arm members. The person using the apparatus is positioned adjacent the connecting element, the arm members are connected to the arcuate members so as to define an included angle related to the field of vision of the person, and the person performs instructional and therapeutic activities using the pole elements and other parts associated therewith.

13 Claims, 15 Drawing Figures

Fig. 1.
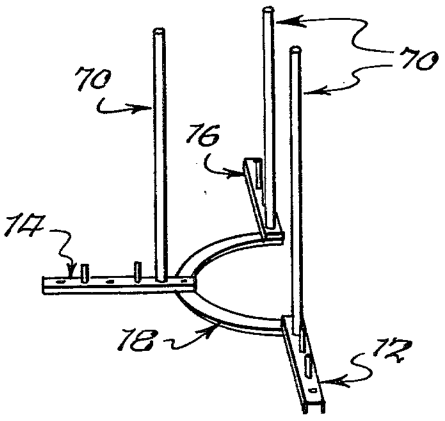
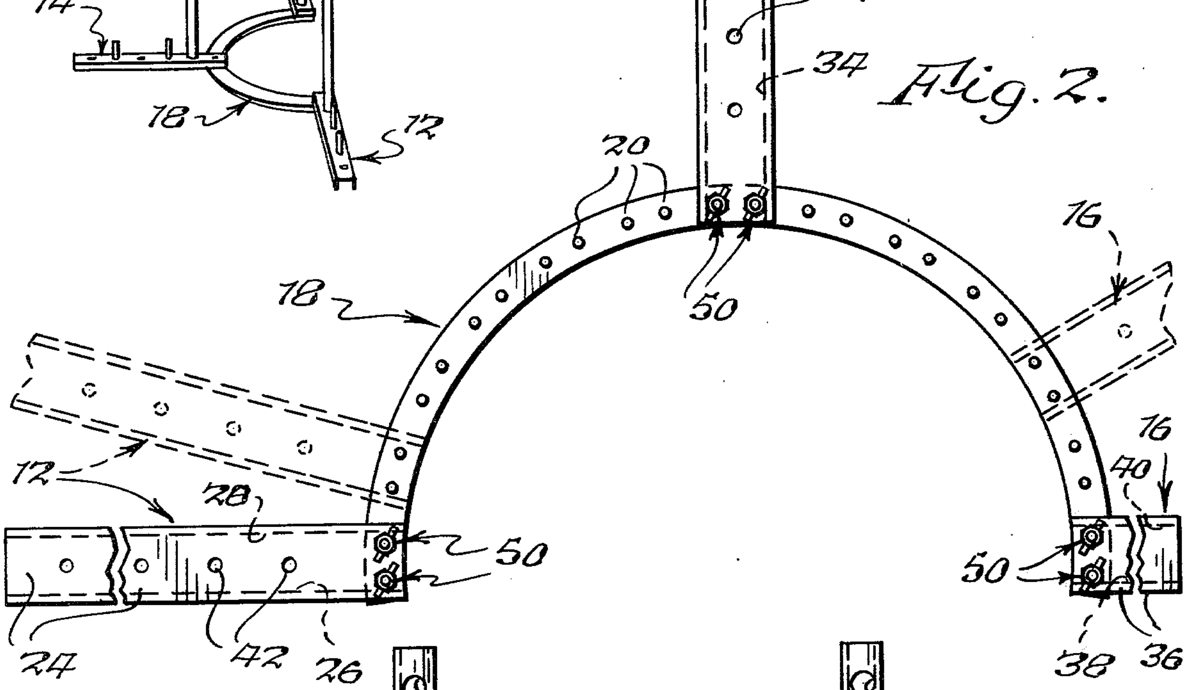
Fig. 2.
Fig. 3.
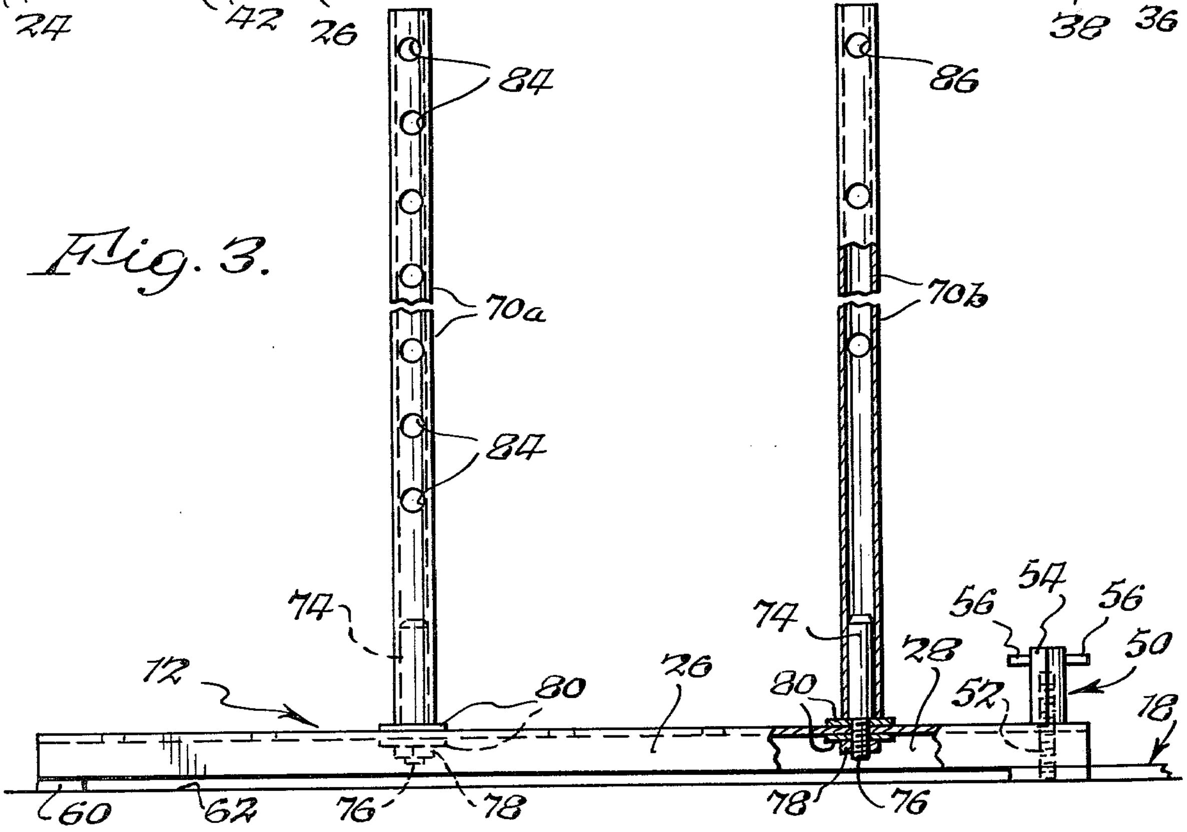

Fig. 14.
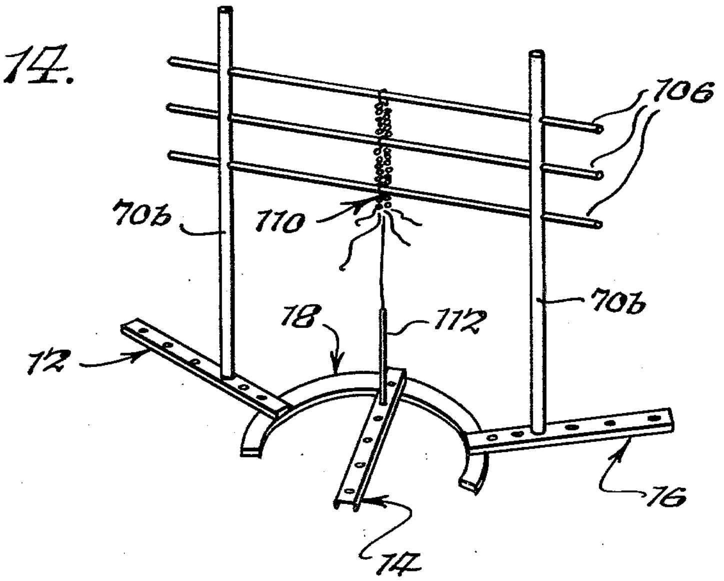
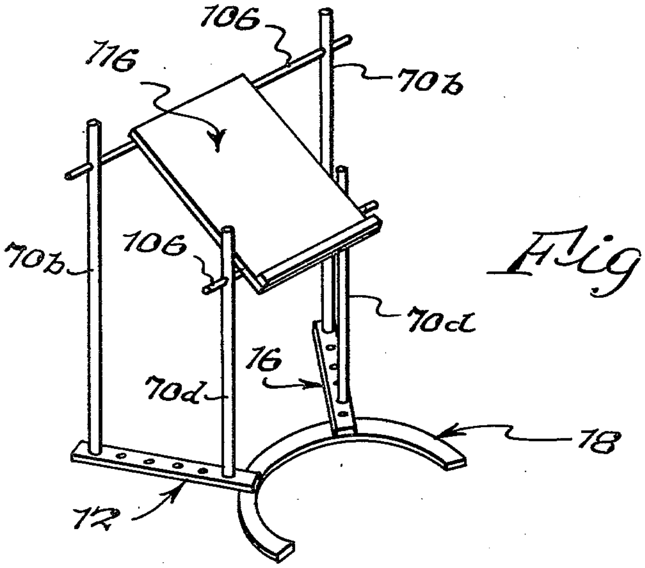
Fig. 15.

THERAPEUTIC APPARATUS

BACKGROUND OF THE INVENTION

This invention relates to the art of therapeutic apparatus, and more particularly to a new and improved apparatus adaptable to therapy for a number of disabilities.

One area of use of the present invention is in physical therapy, although the principles of the present invention can be variously applied. In the design of therapeutic apparatus a number of important considerations exist. A large number of disabilities exist with which persons can be afflicted, either singly or in combination with other disabilities. Thus the apparatus desireably should be readily adaptable to such possibilities. Also, it would be highly desirable to provide such apparatus which has a degree of flexibility enabling the therapist to excerise creativity and imagination in planning activities in which the apparatus is used.

SUMMARY OF THE INVENTION

It is, therefore, a primary object of the present invention to provide new and improved therapeutic apparatus.

It is a more particular object of this invention to provide therapeutic apparatus readily adaptable for use by persons having a wide range of disabilities as well as combinations of disabilities.

It is a further object of this invention to provide such apparatus for use by persons having limited fields of vision.

It is a further object of this invention to provide such apparatus having a degree of flexibility enabling the therapist to exercise creativity and imagination in planning various uses of the apparatus.

It is a further object of this invention to provide such apparatus which is effective in operation and relatively simple in construction.

It is further object of this invention to provide such apparatus which is relatively easy to use and economical to manufacture.

The present invention provides therapeutic apparatus comprising a supporting base provided by at least two and preferably three arm members and each releasably connected at one end to a connecting member and all disposed in substantially the same plane. The arm members extend from the connecting member in a manner defining angles between the arm members, and the connecting member is provided with means for indicating the angles defined between the arm members. At least one pole element is releasably connected at one end to a corresponding arm member, preferably a plurality of pole elements for each arm member, and the pole elements extend all in the same direction and each at substantially a right angle to the plane of the arm members. The base is supported on a floor or similar supporting surface, the user is positioned adjacent the connecting element, the arm members are connected to the connecting member so as to define an included angle indicated on the connecting member which is related to the field of vision of the user, and the user performs instructional and therapeutic activities using the pole elements.

The foregoing and additional advantages and characterizing features of the present invention will become clearly apparent upon a reading of the ensuing detailed description together with the included drawing wherein:

BRIEF DESCRIPTION OF THE DRAWING FIGURES

FIG. 1 is a perspective view of therapeutic apparatus according to the present invention;

FIG. 2 is an enlarged, fragmentary top plan view of the apparatus of FIG. 1 with parts removed;

FIG. 3 is an enlarged, fragmentary side elevational view of the apparatus of FIG. 1 with parts in section;

FIG. 14 is a perspective view of therapeutic apparatus of the present invention set up for another type of activity; and FIG. 15 is a perspective view of the therapeutic apparatus of the present invention set up for another type of activity.

DETAILED DESCRIPTION OF THE ILLUSTRATED EMBODIMENTS

Figure 4:
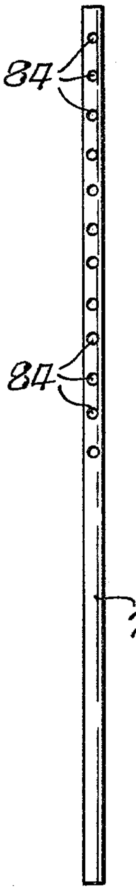
FIGS. 4–8 are side elevational views of pole elements of the apparatus of the present invention.
Figure 5:
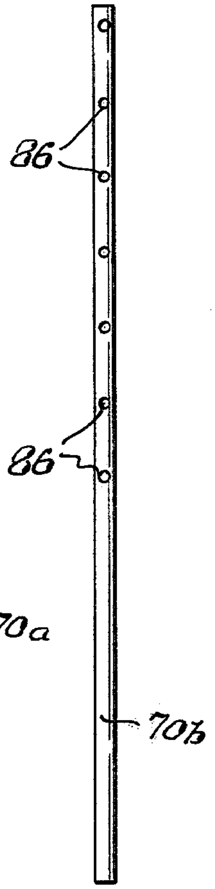

Referring now to FIGS. 1 and 2, the apparatus of the present invention comprises a supporting base or frame including at least two and preferably three elongated arm members generally designated 12, 14, and 16 in FIGS. 1 and 2 and a connecting member 18. The arm members and connecting members are all disposed in substantially the same plane, and the arm members define angles therebetween in a manner which will be described in detail presently. The base or frame defined by the arm members 12, 14, 16 and the connecting member 18 rests on a planar supporting surface such as a floor when the apparatus is in use.

Each of the arm members 12, 14 and 16 is connected at one end to the connecting member 18, and the arm members are located and disposed with one in between the other two. The arm members 12, 14 and 16 extend from connecting member 18 and define therebetween angles up to 180 degrees in the device shown. In particular, the arm member designated 14 may be referred to as an intermediate or middle arm member, and the arm member 12, 16 may be viewed as the outer arm members. Each arm member defines an angle with respect to each of the other two members. Typically, the angles of interest will be between the central arm member 14 and each of two outer arm members 12, 16. Generally, the central or intermediate arm member 14 is connected to the connecting member 18 at a location substantially midway between the ends of the connecting member 18. Each of the two outer arm members 12, 16 then is connected at selected locations along the connecting member so as to define angles with respect to the central arm 14 which vary from a very small acute angle to a right angle. The arm members 12, 14, 16 are of rigid material such as metal, plastic or wood.

In the apparatus shown, the connecting member 18 is of rigid material such as metal, plastic or wood, is substantially solid, and is in the form of a strip or bar of arcuate shape having an arc length equal to the perimeter of a half circle or semi-circle. The member 18 is provided with openings or apertures 20 generally centrally of the width thereof and at spaced locations along the length. The apertures 20 preferably are arranged in pairs which pairs, in turn, are located at constant intervals along the length of the connecting member 18. The spacing between the pairs is such that when an arm are connected to the member 18 at particular ones of the pairs, a definite angular location of the arm is set with respect to the other arms. Thus, arm 14 in the arrangement of FIG. 2 is connected to member 18 at the pair of apertures corresponding to a angle of zero degrees. Each of the arms 12, 16 is connected to member 18 at apertures such that the included angle between arms 12 and 14 is 90° and the included angle between arms 14 and 16 is 90°. The sets or pairs of apertures 20 are located along connecting element 18 at intervals of 15° in the apparatus shown. Thus, the sets or pairs of apertures serve to provide a visual indication of the included angle between arm members 12 and 14 and between arm 16 and arm 14. If desired for further convenience, numerical indicia giving the angle size in degrees can be stamped or otherwise provided on connecting member 18 adjacent each set of apertures 20.

Each of the arm members 12, 14 and 16 in the apparatus shown preferably is in the form of a channel member having a central web and two outer legs or flanges. In particular, arm 12 as shown in FIG. 2 includes a central web 24 and two outer flanges 26, 28. Arm 14 has a central web 30 and two outer flanges 32,34. Arm 16 has a central web 36 and two flanges 38,40. Each of the arms 12, 14 and 16 is disposed with the flanges thereof facing or extending in a direction toward the connecting member 18 and hence toward and contacting the floor or surface upon which the supporting base rests. The arms 12, 14 and 16 are provided with a series of apertures 42, 44 and 46, respectively, in the webs thereof at spaced locations along the longitudinal axes of the respective arm members for a purpose to be described.

The arm members 12, 14 and 16 are removably or releasably connected to the arcuate connecting member 18 each by a pair of fastening elements generally designated 50 in FIG. 2. As shown in more detail in FIG. 3, a typical fastening element 50 includes a threaded rod 52 which is releasably connected at one end into a corresponding threaded aperture or opening 20 in the connecting element 18 and which is disposed at a right angle to the plane of the connecting bar 18. The threaded rod 52 is of sufficient length to extend through an opening provided in the web of the corresponding arm member and to extend beyond the outer surface of the web for a sufficient distance to be securely threaded into an internal longitudinal threaded bore of an element 54 which preferably is cylindrical in shape. The cylindrical element 54 in turn, includes a pair of knob or handle elements 56 to facilitate tightening of the assembly. Thus by turning element 50 manually by hand in one direction it tightens the corresponding arm member against connecting member 18, and turning element 50 in the opposite direction loosens it from removal from the assembly enabling the arm to be re-connected at a new position. Other fastening arrangements can of course be employed. In addition, each of the arm members, for example arm 12 shown in FIG. 3, can be provided with a pad designated 60 in FIG. 3 at the outer end thereof of a thickness substantially equal to the thickness of connecting member 18 to increase the stability of the frame or base as it rests on a floor or supporting surface designated 62 in FIG. 3.

The apparatus of the present invention further comprises a plurality of elongated pole members each adapted to be releasably connected at one end to various ones of the arm members 12, 14 and 16 and to be disposed at an angle, preferably a right angle, to the plane of the frame or supporting base with all of the elongated members extending from the same side of the arms 12, 14 and 16. When the frame comprising arms 12, 14 and 16 and connecting member 18 is supported on a horizontal floor or similar surface, the elongated elements will be disposed generally vertically. In the apparatus illustrated in FIG. 1, three elongated pole elements 70 in the form of rods or tubes are shown each being connected to a corresponding one of the arms 12, 14 and 16. The elongated members generally designated 70 FIG. 1 can be of different overall lengths and can have other variations in structural characteristics such as transverse apertures in some poles and among those having such apertures, different aperture spacing, in a manner which will be described in detail presently. The elongated pole elements preferably are in the form of cylinders or tubes, and FIG. 3 illustrates a preferred arrangement for releasably connecting and supporting each of the tubes on the arm members of the frame. In particular, FIG. 3 illustrates two cylinders of tubes designated **70*a* and 70*b* of different types in terms of number of transverse apertures therein in a manner which will be described presently. The end of each tube is adapted to be fitted onto an upstanding rod member 74 which is releasably connected to the corresponding arm. In particular, a solid cylindrical rod element 74 is provided at one end thereof with a reduced diameter threaded portion 76 which extends through one of the apertures in the arm member, for example an aperture 42 of in web 24 of arm 12 and is secured thereto by an arrangement of nut 78 and washers 80. Rod 74 is disposed at a right angle to the plane of web 24, and has an outer diameter substantially equal to the inner diameter of tube 70*b* whereby the tube end of the tube 70 is fitted onto rod 74 in a firm and tight but releasable manner. As a result, the tube 70*b* is securely releasably connected at the one end to arm 12 and extends such that the longitudinal axis thereof is substantially perpendicular to the plane of the web of arm 12. The axial length of rod 74 extending from web 24 is adequate to provide firm support for the tube 70*b* in an upright position. The tube or cylinder 70*a* is connected to arm 12 by an identical connector member 74. Tube 70*a* illustrated in FIG. 3 includes a plurality of transverse through apertures 84 at spaced locations along the longitudinal axis thereof. Tube 70*b* includes transverse through apertures 86 at spaced locations along the longitudinal axis thereof, the axial spacing between apertures 86 of tube 70*b* being greater than the spacing between apertures 84 of tube 70*a***.

Figure 6:
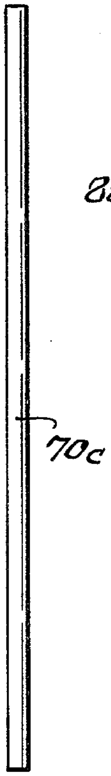
Figure 7:
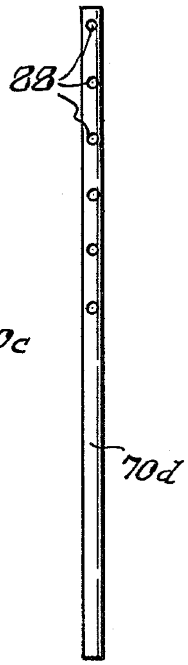
Figure 8:
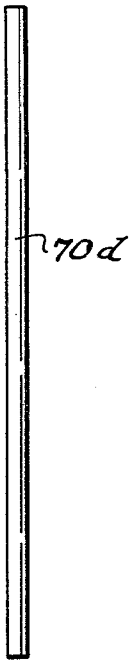

FIGS. 4–8 illustrates the various pole elements 70 which are used in the therapeutic apparatus of the present invention. Pole elements **70*a* and 70*b* shown in FIGS. 4 and 5, respectively, are of the same overall length as previously described. The spacing between the transverse through apertures 84 in pole element 70***a* is greater than the spacing between the transverse through apertures 86 provided in pole element 70*b*. Pole element 70*c* shown in FIG. 6 is of shorter overall length as compared to the pole elements 70*a*, 70*b* and does not include any apertures. Pole elements 70*d* and 70*e* shown in FIGS. 7 and 8, respectively, are of substantially equal lengths and shorter than other pole elements. Pole element 70*d* is provided with transverse through apertures 88 at spaced locations along the length thereof, and the distance or spacing between the apertures 88 of pole element 70*d* is approximately the same as the distance between the apertures 86 provided in pole element 70*b*. Pole element 70*e* does not include any apertures.

Figure 9:
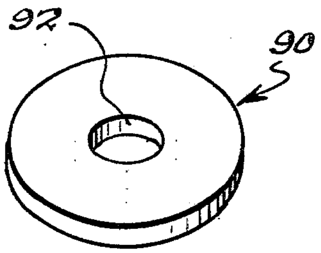
FIG. 9 is a perspective view of a cushioning dise of the apparatus of the present invention.
Figure 10:
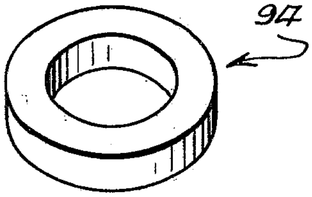
FIG. 10 is a perspective view of an activity element in the form of a ring used in the apparatus of the present invention.

Turning now to FIG. 9, there is shown a cushioning disc 90 of resilient or flexible material such as commercially available foam material, for example polystyrene, having a central opening 92 of a diameter substantially equal to the diameters of the pole elements 70. When the pole elements are connected onto corresponding ones of the arm members, cushioning discs 90 are placed over along the pole elements and located in contact with the adjacent surface of the arm member to cushion and deaden or diminish the sound of ring elements dropped onto the pole elements in a manner which will be described in detail presently. FIG. 10 illustrates such a ring element 94 which is used in various activities provided by the apparatus. A plurality of ring elements are used, each being of wood, plastic or like material. The central opening of each ring element 94 is adequate to allow the ring to be fitted onto the pole elements 70 in a loose fitting relation.

Figure 11:
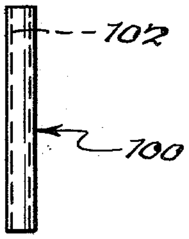
FIG. 11 is a side elevational view of an indicator element in the form of a sleeve used in the apparatus of the present invention.
Figure 12:
FIG. 12 is a side elevational view of a supporting element in the form of a rod used in the apparatus of the present invention.

FIG. 11 illustrates an indicator element 100 in the form of a sleeve having an inner wall 102 of a diameter such that the sleeve can be fitted snugly over the upper end of each of the pole elements 70. The indicator elements 100 typically are color coordinated but can be provided with identifying marks or other indica if desired. The role played by the indicator elements 100 will be described in detail presently. FIG. 12 illustrates a supporting element in the form of a rod or dowel 106 which is used in the apparatus for various activities in a manner which will be described.

The therapeutic apparatus of the present invention is used in the following manner. The apparatus is placed or set up in a position such as that illustrated in FIGS. 1 and 13 with the base or frame including arm members 12, 14 and 16 and connecting member 18 resting on a floor or similar surface so as to be supported thereby. For many activities and exercises, all three of the arms 12, 14 and 16 will be connected, although the apparatus can be used with two of the arms in a manner which will be described presently. The user of the apparatus is positioned, typically seated in a chair, adjacent the connecting member 18 and within the semicircle defined by the arc-shaped member 18. The central or intermediate arm member 14 is located along a line extending substantially perpendicular to a plane or line passing through both eyes of the user. This position of arm member 14 corresponds to a zero degree angular position on connecting member 18 relative to the two outer arm members 12, 16. These outer arm members, in turn, are set at locations determined by such factors as the field of vision of the user and the activity or exercise to be performed. The desired angle is visually perceived by noting the number of pairs of apertures 20 on the connecting member and then fastening the arm member to the desired location. For example, as previously described, the aperture pairs are at spaced locations corresponding to angular increments of about 15 degrees.

Figure 13:
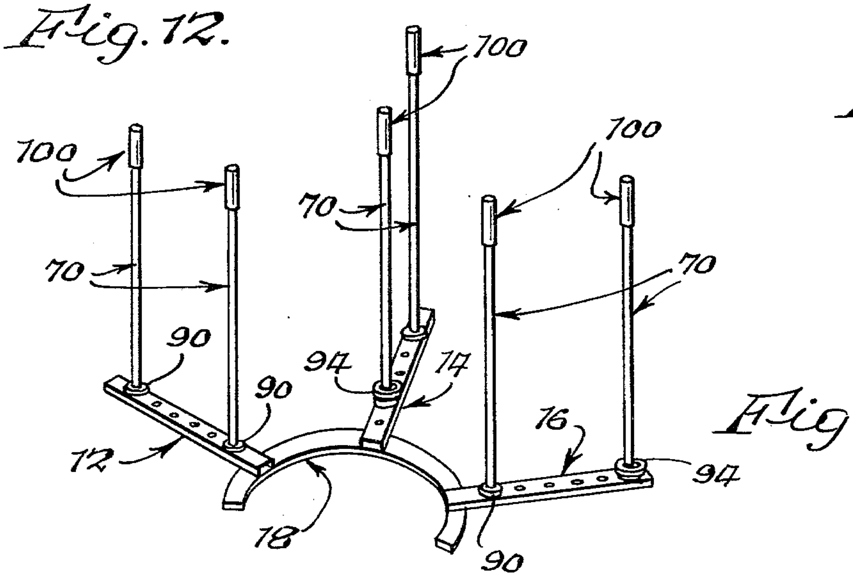
FIG. 13 is a perspective view of therapeutic apparatus of the present invention set up for one type of activity.

In the apparatus arrangement illustrated in FIG. 13, there are two pole elements 70 connected to each of the arm members 12, 14 and 16, and each pole element, in turn, is fitted with a sleeve 100 at the upper end thereof. The sleeves 100 are differentiated by different colors as previously described. Also shown in FIG. 13 a cushioning disc 90 is associated with each pole element 70, in particular being fitted on and along each pole element and located at the lower end thereof in contact with the adjacent surface of the respective arm member. One of the activities which is performed using the apparatus arrangement shown in FIG. 13 is to place particular ones of the rings 94 onto certain pole elements. Rings 94 would be colored in co-ordination with the colors on sleeves 100. Thus, as shown in FIG. 13 the user has already placed a ring 94 on the nearest pole element 70 on arm 14 and has also placed a ring 94 on the farthest pole element 70 on arm 16. Any number of poles 70 can be placed on each arm.

For persons suffering from hemipligic disabilities the apparatus of the present invention is used for various therapeutic activities involving depth perception, color coordination, bilateral activity, eye-hand coordination, general shoulder movement for range of motion, and right-left discrimination. For patients having homonomous hemianopsia or hemianopia the apparatus is adjustable to compensate for vision loss. In particular, one of the basic exercises performed with the apparatus involves color coordination wherein the user matches the rings 94 to particular ones of the poles 70. This is done according to color coordination between the rings 94 and the sleeves 100 fitted on the poles 70. The user matches a ring to a pole and manually places the ring thereon whereupon the ring falls onto the cushioning disc 90 as shown in FIG. 13. The apparatus also is used in depth perception by having the poles set in the arms at specific distances and heights to accomplish this exercise. In particular, the pole elements 70 are provided in various lengths, and they can be connected to each of the arm members 12, 14 and 16 at selected locations therealong corresponding to the apertures provided in the arm elements in the manner previously described. The activity wherein the patient matches rings 94 to the poles 70 also aids in developing eye-hand cordination. In addition, right-left discrimination can be improved or developed by having the patient perform tasks at the direction of the therapist with either hand. By performing the task and reaching either right to left or left to right the midline of the body is crossed. Having the patient perform tasks such as matching rings 94 to poles 70 using both hands can be used to improve bilateral motor cordination. When the patient is performing various activities his range of motion of the upper extremity can be observed and stressed during performance of the task. In this way movements of the shoulders, elbows, wrist and hand can be improved. In addition, by connecting pole elements 70*a*, 70*b* or 70*d* to the arm members, the patient can move his fingers up the poles from aperture to aperture and this exercise aids in developing range of motion of upper extremity.

The capability of adjusting the location of the arm members, particularly the outer arm members 12 and 16 relative to the center arm member, gives the apparatus much versatility with patients suffering from hemionopsia. Thus, the arm member 12 or 14 on the affected side of the patient can be set at the point where vision is lost. The other arm is set at an angle of 90 degrees relative to the central arm. The patient can perform the various tasks using all the arms 12, 14 and 16. To increase the patient's field of vision the angle is slowly increased as the task is perfected. Field of vision is increased by teaching the patient to compensate for vision loss by turning of the head, shoulders and trunk. In other words, although vision is not really increased, the concept of turning to the affected side is achieved. By observing the angle indicated on connecting member 18, the therapist can measure and chart the amount of increase to record improvement.

The apparatus of the present invention thus can be used with patients suffering from a number of different disabilities as well as various combinations of disabilities. It can be adapted to all age groups and disabilities. It can also be used in the testing of disabilities. The versatility provided by the apparatus of the present invention enables the therapist to determine the best use of the apparatus and to use his imagination in adapting the apparatus to the particular problem at hand. When not in use the apparatus can be disassembled for convenient storage. In addition to the foregoing activities described, the apparatus can be used with a number of different types of activities. For example, as shown in FIG. 14 the apparatus is set up to enable a person to work on a macrame or cord knotting project. In this arrangement, the poles **70*b* are used with one pole element being connected to each of the two outer arm members 12 and 16 at the same distance therealong from connecting member 18 as shown in FIG. 14. Then several, for example three dowel or rod elements 106 are placed in the aligned apertures 86 to provide horizontally disposed supporting elements. The macrame or cord material generally designated 110 is secured to the elements 106, and a rod 112 connected at the lower end of the cord is fitted into a projecting element 74 from the central arm 14 for stability. In this instance, the central arm 14 is connected so as to extend within the semicircle defined by the arch-shaped element 18**.

FIG. 15 illustrates still another use of the therapeutic apparatus of the present invention. In this instance it can be used to define an easel or similar arrangement. Only two of the arm members 12 and 16 are used, one of the relatively shorter pole elements **70*d* is connected to each of the arm members at a location close to the connecting member 18 and one of the relatively longer pole elements 70*b* is connected to each arm at an outer location. One rod element 106 is fitted in aligned apertures in the pole elements 70*d* adjacent the upper ends thereof. Similarly, another rod element 106 is fitted in aligned apertures adjacent the upper ends of the pole elements 70*b*. Then, an easel or like supporting surface 116 is rested on the supporting elements 106 and secured thereto in a suitable manner whereby it is in inclined as illustrated in FIG. 15 for use by a person sitting or even standing at a location generally within the semicircle defined by the connecting member 18**.

By way of example, in a illustrative apparatus, each arm member 12, 14 and 16 has an overall length of about 28 inches and a width of about 4 inches. The inner edge of arc-shaped connecting member 18 defines a semicircle having a diameter of 36 inches. The width of member 18 is about 2 inches. Each of the pole elements 70 can be of reinforced fiberglass material having an outer diameter of about 1.0 inch and an inner diameter of about 0.75 inch. Pole elements **70*a*, 70*b* can have an overall length of about 47 inches, with apertures 84 of pole 70*a* having a diameter of about 0.75 inch and center-to-center spacing of about 2 inches and with apertures 86 of pole 70*b* having a diameter of about ⅝ inch and center-to-center spacing of about 4 inches. Poles 70*c* can have an overall length of about 41 inches. Pole elements 70*d* and 70*c* can have an overall length of about 35 inches with apertures 88 of pole 70*d* having a diameter of about ⅝ inch and a center-to-center spacing of about 3.0 inches. Dises 90 can have an outer diameter of about 2.6 inches, an inner diameter of 1.0 inch and a thickness of about 0.45 inch. Rings 94 can have an outer diameter of about 2.6 inches, an inner diameter of about 1.6 inches and a thickness of about 0.5 inch. Sleeves 100**, which can be of plastic, can have a length of about 6.0 inches, an outer diameter of about 1.2 inches and an inner diameter of about 1.0 inch.

It is therefore apparent that the present invention accomplishes its intended objects. While several embodiments of the present invention have been described in detail, this is for the purpose of illustration not limitation.

We claim:

1. Therapeutic apparatus comprising:

(a) a base adapted to rest on a supporting surface such as a floor and comprising at least two arm members and a connecting member all in substantially the same plane, said connecting member comprising a generally arcuate member having two ends and being substantially uniformly configured about an axis substantially perpendicular to said plane and located generally along a line passing through the ends of said connecting member, each of said arm members being connected at one end to said connecting member, said arm members extending from said connecting member in a manner defining therebetween an angle up to 180 degrees;

(b) means for releasably connecting said arm members independently at selected locations along a generally arcuate path on said connecting member for adjusting the angle between said arm members;

(c) means on said connecting member for providing a visual indication of the angle between said arm members; and (d) at least one pole element associated with each of said arm members, each of said pole members being releasably connected at one end to the corresponding arm member, said pole elements extending in the same direction and each at substantially a right angle to the plane of said arm members;

(e) whereby the user of said apparatus is positioned adjacent said connecting member, said arm members are connected to said connecting member so as to define an included angle indicated on said connecting member which is determined by factors such as the activity to be performed and the field of vision of the user, and the user performs instructional and therapeutic activities using said pole elements.

2. Apparatus according to claim 1, further including a third arm member releasably connected at one end to said connecting member at a location between said first-named arm members, said third arm member being disposed in substantially the same place as said first-named arm members and said connecting member, said third arm members extending from said connecting member in a manner defining angles with said first-named arm members.

3. Apparatus according to claim 2, wherein said third arm member is located substantially mid-way between said first-named arm members and each of said angles has a magnitude up to 90 degrees.

4. Apparatus according to claims 2 or 3, further including formations on said connecting member at constant intervals along the length of said member, said formations serving as means for releasably connecting said arm members at selected locations along said connecting member and serving as said means for providing a visual indication of the angle between said arm members.

5. Apparatus according to claim 3, further including formations on said connecting member at constant intervals along the length of said member, said formations serving as said means for releasably connecting said arm members at selected locations along said connecting member and serving as said means for providing a visual indication of the angle between said arm members.

6. Apparatus according to claim 1, wherein said pole elements are provided with transverse apertures at spaced locations therealong.

7. Apparatus according to claim 6, further including at least one rod member adapted to be received in apertures of spaced apart ones of said pole elements whereby said rod member is adapted to be disposed in a direction substantially perpendicular to said pole elements so as to provide support for additional instructional elements.

8. Apparatus according to claim 1, further including visual indicator elements adapted to be fitted onto said pole elements.

9. Apparatus according to claim 1, further including a plurality of ring elements each having an inner diameter greater than the cross sectional dimension of said pole elements.

10. Apparatus according to claim 1, further including a plurality of disc elements of cushioning material each having a central opening of a cross section slightly greater than the cross sectional dimension of said pole elements whereby said disc elements can be fitted onto said pole elements adjacent said arm members.

11. Apparatus according to claim 1, further including formations on said connecting member at constant intervals along the length of said member, said formations serving as said means for releasably connecting said arm members at selected locations along said connecting member and serving as said means for providing a visual indication of the angle between said arm members.

12. Apparatus according to claim 1, further including means for releasably connecting each of said pole elements at selected locations along the corresponding arm member for adjusting the locations of said pole elements.

13. Therapeutic apparatus comprising:

(a) a base adapted to rest on a supporting surface such as a floor and comprising at least two arm members and a connecting member all in substantially the same plane, each of said arm members being releasably connected at one end to said connecting member, said arm members extending from said connecting member in a manner defining therebetween an angle up to 180 degrees;

(b) means on said connecting member for providing a visual indication of the angle between said arm members;

(c) at least one pole element associated with each of said arm members, each of said pole members being releasably connected at one end to the corresponding arm member, said pole elements extending in the same direction and each at substantially a right angle to the plane of said arm members; and (d) each of said arm members being provided with a plurality of projecting members at spaced locations therealong and extending from said arm members at substantially a right angle, each pole element having a hollow end portion adapted to fit over and onto a projecting member in a tight but removable manner, said projecting members serving to releasably connect a plurality of said pole elements;

(e) whereby the user of said apparatus is positioned adjacent said connecting member, said arm members are connected to said connecting member so as to define an included angle indicated on said connecting member which is determined by factors such as the activity to be performed and the field of vision of the user, and the user performs instructional and therapeutic activities using said pole elements.

* * * * *